United States Patent [19]

Holtkamp

[11] Patent Number: Plant 5,383

[45] Date of Patent: Jan. 1, 1985

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinshaft "Optimara", Rees Haffen, Fed. Rep. of Germany

[21] Appl. No.: 424,361

[22] Filed: Sep. 27, 1982

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet named Improved New Jersey characterized by its uniform and vigorous growth habit; strong upright flower stems each of which carries 7–10 large single pink frilled flowers; intensive flower color which does not fade under high temperature conditions; profuse flowering, with the flowers being long lasting and non-dropping, and by its medium green leaves.

1 Drawing Figure

The present invention comprises a new and distinct cultivar of African violet plant, botanically known as *Saintpaulia ionantha,* and hereinafter referred to by the cultivar named Improved New Jersey.

The new cultivar was referred to during the breeding and selection process by the designation D 29/11 pink frilled, and is a product of a planned breeding program. Improved New Jersey was originated from a cross made by me in a controlled breeding program in Isselburg, West Germany. The female or seed parent was a cultivar designated B 224/10 pink, and the male or pollen parent was a cultivar designated B 16/6 pink frilled.

The new cultivar Improved New Jersey was discovered and selected by me in 1978 as a flowering plant within the progeny of the stated cross in a controlled environment in Isselburg, West Germany. Asexual reproduction of the new cultivar by leaf cuttings, as performed by me at Isselburg, West Germany, has demonstrated that the combination of characteristics as herein disclosed for the new cultivar are firmly fixed and are retained through successive generations of asexual reproduction.

Improved New Jersey has not been observed under all possible environmental conditions. The pheno-type may vary significantly with variations in environments such as temperature, light intensity and day length. The following observations, measurements and values describe the new cultivar as grown in Isselburg, West Germany, and Nashville, Tenn., under greenhouse conditions which closely approximate those generally used in commercial practice.

The following traits have been repeatedly observed and are determined to be basic characteristics of Improved New Jersey, which in combination distinguish the new cultivar both from the cultivar New Jersey, disclosed in my U.S. Pat. No. 4,214, and other african violet cultivars known in the industry:

1. Improved New Jersey has a very uniform and vigorous growth habit.

2. Relatively deep pink single frilled flowers, with the center of the flowers being of relatively deeper pink.

3. The flowers are supported on very upright flower stems which curve to the center, thereby providing a tight bouquet above the leaves.

4. The flowering is profuse, with 7–10 and even more single large frilled flowers being carried on each stem.

5. The pink flower color is intensive and does not fade under high temperature conditions.

6. The flowers are long lasting and non-dropping.

7. The leaves are medium green in color, providing a pleasant contrast with the pink flower color.

The accompanying photographic drawing illustrates a typical specimen plant of Improved New Jersey. The colors appearing in the photograph are as true as possible with color illustrations of this type.

In the following description, color references are made to The Royal Horticultural Society Colour Chart (H.C.C) issued by Wilson Colour Ltd., except where general colors or ordinary significance are referred to, and except for the color of the individual flowers, where the color values are based on The Royal Horticultural Society Colour Chart (R.H.S.). Color values were taken at approximately 2 P.M. under natural light conditions at Nashville, Tenn.

BOTANICAL CLASSIFICATION

*Saintpaulia ionantha,* Ramat. cv. Improved New Jersey.

PARENTAGE

Male parent: B 16/6 pink frilled.
Female parent: B 224/10 pink.

PROPAGATION

The new cultivar holds its distinguishing characteristics through successive propagations by leaf cuttings.

PLANT

From 6 cm. to 8 cm. tall when grown in pots, and approximately 25–30 cm. in diameter when fully grown.

Leaves:

*General form.*—Broadly oval with lobes overlapping.
*Diameter.*—5–6 cm.
*Texture.*—Velvet-hairy.
*Aspect.*—Slightly shiny.
*Viens.*—Well pronounced, light green, shiny.
*Color (upperside).*—Parsley green, 00962.
*Color (underside).*—Willow green, 000862/2.

*Petiole.*—Light green on older leaf, purplish on young leaf.

Flowers:

*Buds.*—7–10 and more; ball-shaped.

*Sepals.*—Color: sage green 000861/1. Calyx: flat funnel. Aspect: hairy-spear shape.

Individual flowers:

*Size.*—3–3.5 cm.; relatively large.

*Color.*—Upperside 68A-B, center darker pink. Underside: 68B-C.

*Borne.*—Upright on short pedicel.

Shape: Violet shape, single, frilled.

Corolla: Profuse, tight flowering; full bouquet approximately 10–12 cm. in diameter.

Flowering time: Marketable in 8–10 weeks after potting.

Reproduction organs:

*Anthers.*—2; compound of 4 cells.

*Filaments.*—Styles: color like flower. Pollen color; canary yellow 2.

Roots: Normal development, white when young and active, brownish when older.

Disease resistance: Very good to date.

GENERAL OBSERVATIONS

Improved New Jersey is a very uniform and vigorous grower with strong upright wire-like flower stems each of which carries 7–10 large single pink frilled flowers which are intensive in color and do not fade under higher temperature conditions. The flowers are long lasting and non-dropping.

I claim:

1. A new and distinct cultivar of African violet known by the cultivar name Improved New Jersey, as described and illustrated, and strictly characterized by its uniform and vigorous growth habit; strong upright flower stems each of which carries 7–10 large single pink frilled flowers; intensive flower color which does not fade under high temperature conditions; profuse flowering, with the flowers being long lasting and non-dropping, and by its medium green leaves.

* * * * *

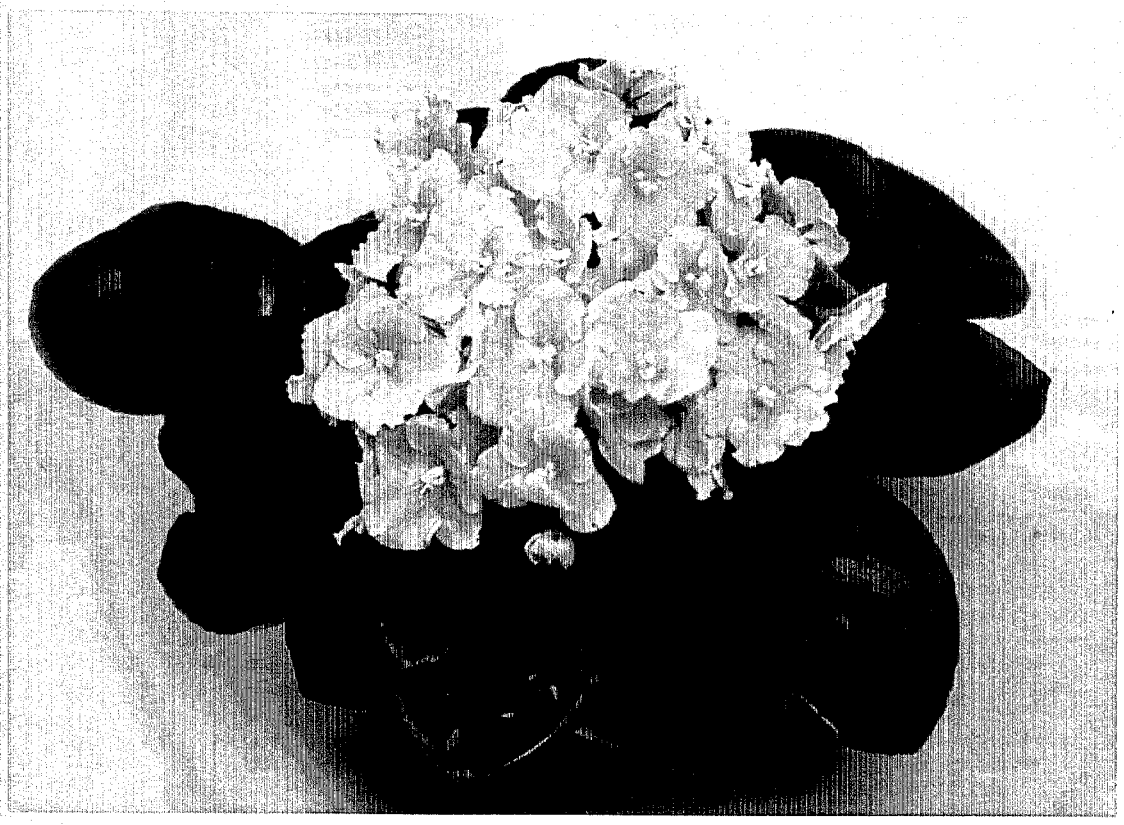

UNITED STATES PATENT OFFICE

CERTIFICATE OF CORRECTION

PATENT NO. : Plant 5383

DATED : January 1, 1985

INVENTOR(S) : Reinhold Holtkamp

It is certified that error appears in the above-identified patent and that said Letters Patent are hereby corrected as shown below:

On the title page Item /54/ should read:

AFRICAN VIOLET PLANT NAMED IMPROVED NEW JERSEY

Signed and Sealed this

Ninth Day of July 1985

[SEAL]

*Attest:*

DONALD J. QUIGG

*Attesting Officer*

*Acting Commissioner of Patents and Trademarks*